(12) United States Patent
Woehr et al.

(10) Patent No.: US 10,080,869 B2
(45) Date of Patent: *Sep. 25, 2018

(54) CATHETER INSERTION DEVICE

(71) Applicant: B. Braun Melsungen AG, Melsungen (DE)

(72) Inventors: Kevin Woehr, Felsberg (DE); Kenneth C. Raines, Bethlehem, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,253

(22) Filed: Sep. 21, 2015

(65) Prior Publication Data

US 2016/0008580 A1   Jan. 14, 2016

Related U.S. Application Data

(63) Continuation of application No. 14/161,169, filed on Jan. 22, 2014, now Pat. No. 9,149,626, which is a
(Continued)

(30) Foreign Application Priority Data

Jul. 4, 2002   (DE) .............................. 202 10 394 U

(51) Int. Cl.
*A61M 25/06* (2006.01)
*A61B 17/34* (2006.01)
(Continued)

(52) U.S. Cl.
CPC ..... *A61M 25/0606* (2013.01); *A61B 17/3415* (2013.01); *A61M 25/0097* (2013.01);
(Continued)

(58) Field of Classification Search
CPC .......... A61M 25/0606; A61M 25/0097; A61M 39/221; A61M 25/0618; A61M 39/0693;
(Continued)

(56) References Cited

U.S. PATENT DOCUMENTS 3,585,996 A   6/1971   Reynolds et al.
3,601,151 A   8/1971   Winnard
(Continued)

FOREIGN PATENT DOCUMENTS

AU         730988 B2   3/2001
AU     2003246358 B2   1/2004
(Continued)

OTHER PUBLICATIONS

Statutory Declaration of Kevin Woehr, Executed on Sep. 15, 2011, in the matter of Australian Patent Application No. 2003246358 and in the matter of Opposition thereto by Terumo Corporation, including Exhibits KW-1 to KW-7 (101 pages).
(Continued)

*Primary Examiner* — Bhisma Mehta
*Assistant Examiner* — Hamza Darb
(74) *Attorney, Agent, or Firm* — Klein, O'Neill & Singh, LLP

(57) ABSTRACT

Embodiments of a catheter insertion device are discussed comprising: an approximately hollow cylindrical catheter sleeve, at whose distal end a catheter is attached; a needle sleeve with a hollow needle, which is attached thereto and which, when ready for use, extends through the catheter sleeve and the catheter, and; a needle protective element that is arranged inside the catheter sleeve while being able to move on the needle. Said needle protective element has an engaging section that engages with an engaging device, which is formed in the vicinity of the needle tip, when the hollow needle is withdrawn from the catheter sleeve. A
(Continued)

check valve is placed inside the catheter sleeve between the catheter and the needle protective element. The hollow needle, when ready for use, extends through said check valve, and the check valve automatically closes once the needle is withdrawn.

20 Claims, 3 Drawing Sheets

Related U.S. Application Data continuation of application No. 14/018,162, filed on Sep. 4, 2013, now Pat. No. 9,149,625, which is a continuation of application No. 13/630,251, filed on Sep. 28, 2012, now Pat. No. 8,540,728, which is a continuation of application No. 13/425,140, filed on Mar. 20, 2012, now Pat. No. 8,337,463, which is a continuation of application No. 12/790,630, filed on May 28, 2010, now Pat. No. 8,328,762, which is a continuation of application No. 10/520,325, filed as application No. PCT/EP03/07073 on Jul. 2, 2003, now Pat. No. 7,736,339.

(51) Int. Cl.
    *A61M 25/00*   (2006.01)
    *A61M 39/22*   (2006.01)
    *A61M 5/32*    (2006.01)
    *A61M 39/06*   (2006.01)

(52) U.S. Cl.
    CPC .... *A61M 25/0618* (2013.01); *A61M 39/0693* (2013.01); *A61M 39/221* (2013.01); *A61M 5/3273* (2013.01); *A61M 39/0606* (2013.01); *A61M 2005/325* (2013.01); *Y10T 29/49826* (2015.01)

(58) Field of Classification Search
    CPC ............ A61M 5/3273; A61M 39/0606; A61M 2005/325; A61M 25/0612; A61M 25/0625; A61M 25/0631; A61M 25/0693; A61B 17/3415; Y10T 29/49826
    See application file for complete search history.

(56) References Cited

U.S. PATENT DOCUMENTS

| | | |
|---|---|---|
| 3,620,500 A | 11/1971 | Santomieri |
| 3,662,754 A | 5/1972 | Halloran |
| 3,727,613 A | 4/1973 | Sorenson et al. |
| 4,143,853 A | 3/1979 | Abramson |
| 4,387,879 A | 6/1983 | Tauschinski |
| 4,449,693 A | 5/1984 | Gereg |
| 4,511,359 A | 4/1985 | Vaillancourt |
| 4,512,766 A | 4/1985 | Vailancourt |
| 4,578,063 A | 3/1986 | Inman et al. |
| 4,673,399 A | 6/1987 | Pruett |
| 4,683,916 A | 8/1987 | Raines |
| 4,762,516 A | 8/1988 | Luther et al. |
| 4,765,588 A | 8/1988 | Atkinson |
| 4,772,266 A | 9/1988 | Groshong |
| 4,790,828 A | 12/1988 | Dombrowski et al. |
| 4,795,432 A | 1/1989 | Karczmer |
| 4,813,938 A | 3/1989 | Raulerson |
| 4,842,591 A * | 6/1989 | Luther ............ A61M 39/0693 285/3 |
| 4,846,809 A | 7/1989 | Sims |
| 4,846,811 A | 7/1989 | Vanderhoof |
| 4,850,961 A | 7/1989 | Wanderer et al. |
| 4,874,377 A | 10/1989 | Newgard et al. |
| 4,883,461 A | 11/1989 | Sawyer |
| 4,917,668 A | 4/1990 | Haindl |
| 4,927,414 A | 5/1990 | Kulli |
| 4,929,235 A | 5/1990 | Merry et al. |
| 4,929,241 A | 5/1990 | Kulli |
| 4,935,010 A | 6/1990 | Cox et al. |
| 4,944,725 A | 7/1990 | McDonald |
| 4,944,728 A | 7/1990 | Carrell et al. |
| 4,952,207 A | 8/1990 | Lemieux |
| 4,964,854 A | 10/1990 | Luther |
| 4,966,586 A | 10/1990 | Vaillancourt |
| 4,978,344 A | 12/1990 | Dombrowski et al. |
| 5,007,901 A | 4/1991 | Shields |
| 5,010,925 A | 4/1991 | Atkinson et al. |
| 5,051,109 A | 9/1991 | Simon |
| 5,053,014 A | 10/1991 | Van Heugten |
| 5,053,017 A | 10/1991 | Chamuel |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,098,393 A | 3/1992 | Amplatz et al. |
| 5,108,374 A | 4/1992 | Lemieux |
| 5,116,021 A | 5/1992 | Faust et al. |
| 5,127,905 A | 7/1992 | Lemieux |
| 5,135,489 A | 8/1992 | Jepson et al. |
| 5,135,504 A | 8/1992 | McLees |
| 5,147,327 A | 9/1992 | Johnson |
| 5,152,751 A | 10/1992 | Kozlowski |
| 5,154,703 A | 10/1992 | Bonaldo |
| 5,156,596 A | 10/1992 | Balbierz et al. |
| 5,158,554 A | 10/1992 | Jepson et al. |
| 5,180,370 A | 1/1993 | Gillespie |
| 5,183,468 A | 2/1993 | McLees |
| 5,188,607 A | 2/1993 | Wu |
| 5,195,980 A | 3/1993 | Catlin |
| 5,215,525 A | 6/1993 | Sturman |
| 5,215,528 A | 6/1993 | Purdy et al. |
| 5,234,410 A | 8/1993 | Graham et al. |
| 5,242,393 A | 9/1993 | Brimhall et al. |
| RE34,416 E | 10/1993 | Lemieux |
| 5,269,771 A | 12/1993 | Thomas et al. |
| 5,300,033 A | 4/1994 | Miller |
| 5,300,045 A | 4/1994 | Plassche, Jr. |
| 5,312,355 A | 5/1994 | Lee |
| 5,322,517 A | 6/1994 | Sircom et al. |
| 5,328,482 A | 7/1994 | Sircom et al. |
| 5,330,435 A | 7/1994 | Vaillancourt |
| 5,334,158 A | 8/1994 | McLees |
| 5,334,159 A | 8/1994 | Turkel |
| 5,334,161 A | 8/1994 | Gurmarnik |
| 5,344,408 A | 9/1994 | Partika |
| 5,348,544 A | 9/1994 | Sweeney et al. |
| 5,352,205 A | 10/1994 | Dales et al. |
| 5,380,305 A | 1/1995 | Ghouri |
| 5,405,323 A | 4/1995 | Rogers et al. |
| 5,405,336 A | 4/1995 | Austin et al. |
| 5,409,461 A | 4/1995 | Steinman |
| 5,419,766 A | 5/1995 | Chang et al. |
| 5,423,766 A | 6/1995 | Di Cesare |
| 5,423,799 A | 6/1995 | Shin |
| 5,454,790 A | 10/1995 | Dubrul |
| 5,456,675 A | 10/1995 | Wolbring et al. |
| 5,458,640 A | 10/1995 | Gerrone |
| 5,458,658 A | 10/1995 | Sircom |
| 5,487,728 A | 1/1996 | Vaillancourt |
| 5,501,675 A | 3/1996 | Erskine |
| 5,538,508 A | 7/1996 | Steyn |
| 5,558,651 A | 9/1996 | Crawford et al. |
| 5,562,630 A | 10/1996 | Nichols |
| 5,562,633 A | 10/1996 | Wozencroft |
| 5,573,516 A | 12/1996 | Tyner |
| 5,584,809 A | 12/1996 | Gaba |
| 5,601,536 A | 2/1997 | Crawford et al. |
| 5,613,663 A * | 3/1997 | Schmidt ............ A61M 39/26 251/149.2 |
| 5,634,913 A | 6/1997 | Stinger |
| 5,651,772 A | 7/1997 | Arnett |
| 5,662,610 A | 9/1997 | Sircom |
| 5,688,253 A | 11/1997 | Paradis |
| 5,697,907 A | 12/1997 | Gaba |

(56) References Cited

U.S. PATENT DOCUMENTS

| | | |
|---|---|---|
| 5,718,688 A | 2/1998 | Wozencroft |
| 5,725,503 A | 3/1998 | Arnett |
| 5,738,144 A | 4/1998 | Rogers |
| 5,749,857 A | 5/1998 | Cuppy |
| 5,749,859 A | 5/1998 | Powell |
| 5,755,709 A | 5/1998 | Cuppy |
| 5,779,681 A | 7/1998 | Bonn |
| D397,434 S | 8/1998 | Pike |
| 5,792,122 A | 8/1998 | Brimhall et al. |
| 5,817,069 A | 10/1998 | Arnett |
| 5,830,189 A | 11/1998 | Chang |
| 5,843,046 A | 12/1998 | Motisi et al. |
| 5,851,196 A | 12/1998 | Arnett |
| 5,853,393 A | 12/1998 | Bogert |
| 5,858,002 A | 1/1999 | Jesch |
| 5,865,806 A | 2/1999 | Howell |
| 5,879,337 A | 3/1999 | Kuracina et al. |
| 5,911,705 A | 6/1999 | Howell |
| 5,911,710 A | 6/1999 | Barry et al. |
| 5,935,104 A | 8/1999 | Janek et al. |
| 5,954,698 A | 9/1999 | Pike |
| 5,961,497 A | 10/1999 | Larkin |
| 5,967,490 A | 10/1999 | Pike |
| 5,971,957 A | 10/1999 | Luther et al. |
| 6,001,080 A | 12/1999 | Kuracina et al. |
| 6,004,294 A | 12/1999 | Brimhall et al. |
| 6,077,244 A | 6/2000 | Botich et al. |
| 6,080,137 A | 6/2000 | Pike |
| 6,117,108 A | 9/2000 | Woehr et al. |
| 6,171,287 B1 | 1/2001 | Lynn et al. |
| 6,203,527 B1 | 3/2001 | Zadini et al. |
| 6,213,978 B1 | 4/2001 | Voyten |
| 6,221,047 B1 | 4/2001 | Greene et al. |
| 6,228,060 B1 | 5/2001 | Howell |
| 6,273,869 B1 | 8/2001 | Vaillancourt |
| 6,287,278 B1 | 9/2001 | Woehr et al. |
| 6,322,537 B1 | 11/2001 | Chang |
| 6,352,520 B1 | 3/2002 | Miyazaki |
| 6,379,333 B1 | 4/2002 | Brimhall et al. |
| 6,379,372 B1 | 4/2002 | Dehdashtian et al. |
| 6,443,927 B1 | 9/2002 | Cook |
| 6,443,929 B1 | 9/2002 | Kuracina et al. |
| 6,485,468 B2 | 11/2002 | Vojtasek |
| 6,506,181 B2 | 1/2003 | Meng et al. |
| 6,533,759 B1 | 3/2003 | Watson et al. |
| 6,585,704 B2 | 7/2003 | Luther et al. |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,629,959 B2 | 10/2003 | Kuracina et al. |
| 6,652,486 B2 * | 11/2003 | Bialecki ............ A61M 25/0618 604/110 |
| 6,652,490 B2 | 11/2003 | Howell |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |
| 6,764,468 B1 | 7/2004 | East |
| 6,860,871 B2 | 3/2005 | Kuracina et al. |
| 6,883,778 B1 | 4/2005 | Newton et al. |
| 6,902,546 B2 | 6/2005 | Ferguson |
| 6,916,311 B2 | 7/2005 | Vojtasek |
| 6,958,055 B2 | 10/2005 | Donnan et al. |
| 6,972,002 B2 | 12/2005 | Thorne |
| RE38,996 E | 2/2006 | Crawford et al. |
| 7,008,404 B2 | 3/2006 | Nakajima |
| 7,125,396 B2 | 10/2006 | Leinsing et al. |
| 7,374,554 B2 | 5/2008 | Menzi et al. |
| 7,500,965 B2 | 3/2009 | Menzi et al. |
| 7,524,306 B2 | 4/2009 | Botich et al. |
| 7,635,352 B2 | 12/2009 | Adams |
| 7,651,476 B2 | 1/2010 | Kohler |
| 7,736,339 B2 | 6/2010 | Woehr et al. |
| 7,959,613 B2 | 6/2011 | Rhad et al. |
| 8,079,979 B2 | 12/2011 | Moorehead |
| 8,308,691 B2 | 11/2012 | Woehr et al. |
| 8,328,762 B2 | 12/2012 | Woehr et al. |
| 8,333,735 B2 * | 12/2012 | Woehr ............... A61M 25/0618 604/164.08 |
| 8,337,463 B2 * | 12/2012 | Woehr ............... A61M 25/0618 604/164.08 |
| 8,382,718 B2 | 2/2013 | Woehr |
| 8,460,247 B2 | 6/2013 | Woehr et al. |
| 8,469,928 B2 | 6/2013 | Stout et al. |
| 8,540,728 B2 | 9/2013 | Woehr et al. |
| 8,597,249 B2 | 12/2013 | Woehr et al. |
| 9,149,626 B2 | 10/2015 | Woehr et al. |
| 2001/0004686 A1 | 6/2001 | Huet |
| 2001/0041872 A1 | 11/2001 | Paul, Jr. |
| 2001/0053895 A1 | 12/2001 | Vaillancourt |
| 2002/0128604 A1 | 9/2002 | Nakajima |
| 2002/0128605 A1 | 9/2002 | Miller et al. |
| 2002/0169418 A1 | 11/2002 | Menzi et al. |
| 2003/0060771 A1 | 3/2003 | Bialecki et al. |
| 2003/0199827 A1 | 10/2003 | Thorne |
| 2004/0044313 A1 | 3/2004 | Nakajima |
| 2004/0116856 A1 | 6/2004 | Woehr et al. |
| 2004/0225260 A1 | 11/2004 | Villa et al. |
| 2005/0043684 A1 | 2/2005 | Basta et al. |
| 2005/0075609 A1 | 4/2005 | Latona |
| 2005/0182363 A1 | 8/2005 | Kulli |
| 2006/0155245 A1 | 7/2006 | Woehr |
| 2006/0178635 A1 | 8/2006 | Callaway |
| 2006/0200080 A1 | 9/2006 | Abulhaj |
| 2007/0038182 A1 | 2/2007 | Bialecki et al. |
| 2007/0038186 A1 | 2/2007 | Sutton et al. |
| 2007/0196414 A1 | 8/2007 | Hammarsten et al. |
| 2014/0135702 A1 | 5/2014 | Woehr et al. |
| 2016/0008580 A1 | 1/2016 | Woehr et al. |

FOREIGN PATENT DOCUMENTS

| | | |
|---|---|---|
| AU | 783650 B2 | 11/2005 |
| CA | 2133053 | 3/1995 |
| DE | 2817102 | 10/1979 |
| DE | 30 00 903 A1 | 1/1980 |
| DE | 31 00 622 A1 | 4/1980 |
| DE | 32 10 148 A1 | 9/1983 |
| DE | 44 34 569 A1 | 3/1995 |
| DE | 691 15 064 | 8/1996 |
| DE | 195 45 452 | 11/1996 |
| DE | 196 39 870 | 12/1997 |
| DE | 299 21 084 | 2/2000 |
| DE | 199 15 342 | 10/2000 |
| DE | 199 55 445 | 6/2001 |
| DE | 201 04 539 U1 | 1/2002 |
| DE | 695 28 043 | 5/2003 |
| EP | 0352928 | 1/1990 |
| EP | 0 414 997 A1 | 4/1990 |
| EP | 0475375 | 3/1992 |
| EP | 0 554 841 A1 | 8/1993 |
| EP | 0 747 084 A2 | 12/1996 |
| EP | 0747085 | 12/1996 |
| EP | 0 799 626 A1 | 10/1997 |
| EP | 1 101 508 A2 | 5/2001 |
| EP | 1 101 508 A3 | 8/2001 |
| EP | 1 180 381 A1 | 2/2002 |
| EP | 0 746 359 | 9/2002 |
| EP | 1 240 916 B1 | 9/2002 |
| EP | 1 374 942 A1 | 1/2004 |
| EP | 1 374 942 B1 | 1/2004 |
| EP | 1 003 588 | 11/2004 |
| EP | 1 545 681 | 1/2008 |
| EP | 1 911 485 | 4/2008 |
| EP | 2292925 | 3/2011 |
| ES | 2254280 | 6/2006 |
| FR | 2794591 | 12/2000 |
| GB | 2 118 440 A | 11/1983 |
| GB | 2292925 | 3/1996 |
| JP | 6-154236 A | 6/1994 |

(56) References Cited

FOREIGN PATENT DOCUMENTS

| | | |
|---|---|---|
| JP | H07-503172 | 4/1995 |
| JP | 8-219314 A | 8/1996 |
| JP | 09-099096 A | 4/1997 |
| JP | H10-57497 | 3/1998 |
| JP | 2000-504973 | 4/2000 |
| JP | 2001-514943 | 9/2001 |
| JP | 2002-000727 A | 1/2002 |
| JP | 2002102345 | 4/2002 |
| JP | 2002-126080 | 5/2002 |
| WO | WO 90/12606 | 11/1990 |
| WO | WO 93/05840 | 4/1993 |
| WO | WO 1995/022364 | 8/1995 |
| WO | WO 97/45151 | 12/1997 |
| WO | WO 98/30268 | 7/1998 |
| WO | WO 98/53875 | 12/1998 |
| WO | WO 99/08742 | 2/1999 |
| WO | WO 99/26682 | 6/1999 |
| WO | WO 01/07103 | 2/2001 |
| WO | WO 2001/012249 | 2/2001 |
| WO | WO 03/011381 A1 | 2/2003 |
| WO | WO 03/011383 | 2/2003 |
| WO | WO 2004/004819 A1 | 1/2004 |

OTHER PUBLICATIONS

Statutory Declaration of William Samuel Hunter, Executed and Notarized on May 11, 2010, in the matter of Australian Patent Application No. 2003246358 and in the matter of Opposition thereto by Terumo Corporation (43 pages).

Statutory Declaration of Noel J. Akers, Executed and Notarized on Aug. 17, 2011, in the matter of Australian Patent Application No. 2003246358, including Exhibit NJA-1 (48 pages).

Annex 1: Facts and Arguments to the Notice of Opposition to a European Patent; Opponent Smith Medical ASD Inc.; Patentee B. Braun Melsungen AG for Opposed Patent No. EP 1 545 681 B1; dated Oct. 21, 2008 (133 pages).

Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Jan. 27, 2011 (77 pages).

Response to Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Oct. 21, 2011 (86 pages).

Patent Abstracts of Japan; entitled "Indwelling Puncture Needle With Wing Having Branching Part", Application No. 11-021665, Publication No. 2000-217925; Published Aug. 8, 2000, Applicant Hanako Medical KK (3 pages).

Patent Abstracts of Japan; entitled "Safe Indwelling Needle", Application No. 2000-078335, Publication No. 2001-259029, Published Sep. 25, 2001, Applicant Medikit KK (7 pages).

Patent Abstracts of Japan; entitled "Safety Indwelling Needle", Application No. 2000-182911, Publication No. 2002-000727, Published Jan. 8, 2002, Applicant Medikit KK (4 pages).

Patent Abstracts of Japan; entitled "Indwelling Needle Structure", Applicant No. 2001-363865, Publication No. 2003-175112, Published Jun. 24, 2003, Applicant Mitsubishi Pencil Co LTD (5 pages).

Patent Abstracts of Japan; entitled "Indwelling Needle Structure and Seal Material Used Therefore", Application No. 2005-035112, Publication No. 2005261938 A, Published Sep. 29, 2005, Applicant JMS Co LTD (5 pages).

Patent Abstracts of Japan; entitled "Indwelling Needle", Application No. 2004-143931, Publication No. 2005-323762, Published Nov. 24, 2005, Applicant Medikit KK (4 pages).

Patent Abstracts of Japan; entitled "Indwelling Needle", Application No. 1996-0040652, Publication No. 9206375, Published Aug. 12, 1997, Applicant: Togo Medikit KK (2 pages).

"Conical Fittings With 6% (Luer) Taper for Syringes, Needles and Certain Other Medical Euipment—Part 2: Lock fittings," International Standar, ISO 594-2, second edition, 1998, pp. 1-11, Technical Committee ISO/TC 84, Switzerland.

Office Action dated May 29, 2007 from corresponding U.S. Appl. No. 10/520,325, filed Sep. 12, 2005.

Final Office Action dated Nov. 14, 2007 from corresponding U.S. Appl. No. 10/520,325, filed Sep. 12, 2005.

Office Action dated Sep. 26, 2008 from corresponding U.S. Appl. No. 10/520,325, filed Sep. 12, 2005.

Final Office Action dated Mar. 30, 2009 from corresponding U.S. Appl. No. 10/520, 325, filed Sep. 12, 2005.

Final Office Action dated Jan. 19, 2010 from corresponding U.S. Appl. No. 10/520,325, filed Sep. 12, 2005.

Notice of Allowance dated Feb. 25, 2010 from corresponding U.S. Appl. No. 10/520,325, filed Sep. 12, 2005.

Office Action dated Jun. 21, 2011 from corresponding U.S. Appl. No. 12/790,630, filed May 28, 2010.

Office Action dated Aug. 8, 2011 from corresponding U.S. Appl. No. 12/790,630, filed May 28, 2010.

Office Action dated Oct. 9, 2012 from corresponding U.S. Appl. No. 12/790,630, filed May 28, 2010.

Notice of Allowance dated Nov. 7, 2012 from corresponding U.S. Appl. No. 12/790,630, filed May 28, 2010.

Office Action dated Oct. 10, 2012 from corresponding U.S. Appl. No. 13/425,140, filed Mar. 20, 2012.

Notice of Allowance dated Nov. 7, 2012 from corresponding U.S. Appl. No. 13/425,140, filed Mar. 20, 2012.

Office Action dated Mar. 22, 2013 from corresponding U.S. Appl. No. 13/630,251, filed Sep. 28, 2013.

Notice of Allowance dated Jun. 20, 2013 from corresponding U.S. Appl. No. 13/630,251, filed Sep. 28, 2013.

Office Action dated Aug. 29, 2013 from corresponding U.S. Appl. No. 13/630,251, filed Sep. 28, 2013.

Re-Examination Report dated Aug. 30, 2013 from related Australian Application No. 2003246368 (5 pages).

Response to Re-Examination Report Aug. 30, 2013, filed Oct. 3, 2013 from related Australian Application No. 2003246368 (8 pages).

Office Action dated Dec. 19, 2014 from corresponding U.S. Appl. No. 14/018,162, filed Sep. 4, 2013.

Office Action dated Dec. 26, 2014 from corresponding U.S. Appl. No. 12/161,169, filed Jan. 22, 2014.

Official Action on corresponding foreign application (MX Application No. MX/a/2015/015133) from the Mexican Institute of the Industrial Property dated Jan. 23, 2018.

Official Action on corresponding foreign application (MX Application No. MX/a/2015/015134) from the Mexican Institute of the Industrial Property dated Jan. 31, 2018.

Official Action on corresponding foreign application (MX Application No. MX/a/2015/015136) from the Mexican Institute of the Industrial Property dated Feb. 8, 2018.

ISO 594-1, "Conical fittings with a 6% (Luer) taper for syringes, needles and certain other medical equipment—Part 1: General Requirements", International Standard (ISO), 594-1, First edition, Jun. 15, 1986, pp. 1-7.

David Holthaus, "Suppliers heed call for protective products", Hospitals, The Magazine for Health Care Executives, Sep. 20, 1987, pp. 72-73.

"Joint Advisory Notice: Department of Labor/Department of Health and Human Services; HBV/HIV", Federal Register, vol. 52, No. 210, Oct. 30, 1987, pp. 41818-41824.

Federal Register, Part II, Department of Labor, Occupational Safety and Health Administration, "Occupational Exposure to Bloodborne Pathogens; Final Rule", 29 CFR Part 1910.1030, vol. 56, No. 235, Dec. 6, 1991, 180 pages.

Chiarello et al., "N.Y. State, Department of Health, Pilot Study of Needlestick Prevention Devices, Report to the New York State Legislature", Mar. 1992, 73 pages, Part 1 of 2.

Chiarello et al., "N.Y. State, Department of Health, Pilot Study of Needlestick Prevention Devices, Report to the New York State Legislature", Mar. 1992, 77 pages, Part 2 of 2.

FDA Safety Alert, "Needlestick and Other Risks from Hypodermic Needles on Secondary I.V. Administration Sets—Piggyback and Intermittent I.V.", https://www.osha.gov/SLTC/bloodbornepathogens/fdaletter.html, Apr. 16, 1992.

(56) References Cited

OTHER PUBLICATIONS

Chiarello, "Selection of needlestick prevention devices: A conceptual framework for approaching product evaluation", American Journal of Infection Control, vol. 23, No. 6, Dec. 1995, pp. 386-395.
Judy Terry et al., "Intravenous Therapy Clinical Principles and Practice", W.B. Saunders Company, 1995, pp. 317-324.
ISO 10555-5, "Sterile, single-use intravascular catheters—Part 5: Over-needle peripheral catheters", International Standard (ISO) 10555-5, First edition, Jun. 15, 1996, pp. 1-14.
Lawrence F. Leslie et al, "Needle Puncture Resistance of Surgical Gloves, Finger Guards, and Glove Liners", Journal of Biomedical Materials Research (Applied Biomaterials), vol. 33, John Wiley & Sons, Inc., 1996, pp. 41-46.
Julie Steele, "Practical I.V. Therapy", $2^{nd}$ edition, Springhouse Corporation, Springhouse, Pennsylvania, 1996, pp. 27-56.
Hanrahan & Reutter, "A critical review of the literature on sharps injuries: epidemiology, management of exposures and prevention", Journal of Advanced Nursing, vol. 25, Blackwell Science, Ltd., 1997, pp. 144-154.
ECRI, "Needlestick-Prevention Devices", Health Devices, Oct. 1999, vol. 28, No. 10, 9 pages.
"Preventing Needlestick Injuries in Health Care Settings", National Institute for Occupational Safety and Health ("NIOSH") Alert issued by the Centers for Disease Control and Prevention ("CDC"), Pub No. 2000-108, Nov. 1999, 29 pages.
Claus M. Muth & Erik S. Shank, "Gas Embolism", The New England Journal of Medicine, vol. 342, No. 7, Massachusetts Medical Society, Feb. 17, 2000, pp. 476-482.
"Needlestick Safety and Prevention Act", Public Law No. 106-430, Nov. 6, 2000, 114 Stat. 1901-1905.
"Resilience", Stedman's Medical Dictionary, 27th Edition, Lippincott Williams & Wilkins, Balitimore, MD, 2000, 5 pages.
Centers for Disease Control and Prevention, "Updated U.S. Public Health Service Guidelines for the Management of Occupational Exposures to HBV, HCV, and HIV and Recommendations for Postexposure Prophylaxis", Morbidity and Mortality Weekly Report, U.S. Department of Health and Human Services, CDC, Atlanta, GA, vol. 50, No. RR-11, Jun. 29, 2001, 67 pages.
Judy Hankins, BSN, CRNI, et al., "Infusion Therapy in Clinical Practice", 2nd edition, W.B. Saunders Company, 2001, pp. 313-318; 344-347.
Osha Fact Sheet, "OSHA's Bloodborne Pathogens Standard", U.S. Dept. of Labor Reference Guide, 2001, 2 pages.
Osha, "Bloodborne Pathogens" Standard No. 1910.1030, 2001, 24 pages.
Lynn Dianne Phillips, "Manual of I.V. Therapeutics", $3^{rd}$ edition, F.A. Davis Company, Philadelphia, PA, 2001, 98 pages, Part 1.
Lynn Dianne Phillips, "Manual of I.V. Therapeutics", $3^{rd}$ edition, F.A. Davis Company, Philadelphia, PA, 2001, 111 pages, Part 2.
Weinstein, "Plumer's Principles & Practices of Intravenous Therapy", $7^{th}$ edition, Lippincott, 2001, Chapter 11, pp. 193-230.
Asai et al., "Efficacy of catheter needles with safeguard mechanisms", Anaesthesia, 2002, pp. 572-577, vol. 57, Blackwell Science Ltd.
Andrea Mummery, "Be sharp, be safe", Occupational Health, vol. 54, No. 9, Sep. 2002, 6 pages.
Saladow, "The use of vascular access devices with needle safety features", JVAD, Fall 2002, pp. 41-44.
Fran Powers, "Effectively Evaluating and Converting Your Organization to the Use of Infusion Safety Products", Journal of Infusion Nursing, vol. 25, No. 6S, Nov./Dec. 2002, pp. S10-S14.
Trim, JC, "A review of needle-protective devices to prevent sharps injuries", Clinical, British Journal of Nursing, vol. 13, No. 3, 2004, pp. 144-153.
FDA, Guidance for Industry and FDA Staff—"Medical Devices with Sharps Injury Prevention Features", U.S. Department of Health and Human Services, FDA, Center for Devices and Radiological Health, Aug. 9, 2005, pp. 1-17.
McKean, "Resilient", The New Oxford American Dictionary, second edition, Oxford University Press, 2005, 5 pages.
Rivera et al., "The history of peripheral intravenous catheters: How little plastic tubes revolutionized medicine", Acta Anaesthesiologica Belgica, vol. 56, No. 3, 2005, pp. 271-282.
U.S. Appl. No. 61/127,742 to Stephens, filed May 14, 2008, 45 pages.
Definition of "arm", www.engineering-dictionary.org, 2008.
B. Braun Introcan Safety IV Catheter, B. Braun Medical Inc., 2009.
"Top 10 Health Technology Hazards for 2011", Health Devices, vol. 39, Issue 11, Nov. 2010, ECRI Institute, pp. 386-398.
BD Saf-T-Intima, Beckton, Dickinson and Company, Jan. 2013.
OSHA—Compliance with bloodborne pathogens standard, Premier Safety Institute 2015, http://www.premiersafetyinstitute.org/safety-topics-az/needlestick-prevention/oshacompliance-with-bloodborne-pathogens-standard/.
B. Braun Interventional Systems Inc., Accel™ Valved Safety Centesis Catheter With Introcan Safety™ Technology, 2016.
BD Medical, BD Insyte Autoguard BC Shielded IV Catheter with Blood Control Technology, Beckton, Dickinson and Company, 2016.
B. Braun Medical Inc., MINI-SPIKE® Dispensing Pins, 2017, http://www.bbraunusa.com/products.html?prid=PRID00006971.
BD Insyte Autoguard Shielded IV Catheter, 2017, http://www.bd.com/en-us/offerings/capabilities/infusion/iv-catheters/bd-insyte-autoguard-shielded-iv-catheter.
The Medikit Supercath Z3V, http://www.medikit.co.jp/english/product/p1.html; 2017.
First Office Action on corresponding foreign application (MX Application No. MX/a/2015/015133) from the Mexican Intellectual Property Office dated Aug. 4, 2017.
Second Office Action on corresponding foreign application (MX Application No. MX/a/2015/015134) from the Mexican Intellectual Property Office dated Aug. 14, 2017.
IPR Trial No. IPR2017-01586, U.S. Pat. No. 8,328,762; Petition for Inter Partes Review of Claims 18, 22, 25 of U.S. Pat. No. 8,328,762 Under 35 U.S.C. 312 and 37 C.F.R. 42.104; USPTO PTAB; *Becton, Dickinson and Company v. B. Braun Melsungen AG*; Jun. 16, 2017; 60 pages.
Case IPR2017-01586, U.S. Pat. No. 8,328,762 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
Case IPR2017-01586, U.S. Pat. No. 8,328,762 B2; Decision Institution of Inter Partes Review 37 C.F.R. 42.108; USPTO PTAB; *Becton, Dickinson and Company v. B. Braun Melsungen AG*, Dec. 15, 2017; Paper No. 8; 39 pages.
IPR Trial No. IPR2017-01585, U.S. Pat. No. 8,337,463; Petition for Inter Partes Review of Claims 1, 2, 10, 12, 25, 28 of U.S. Pat. No. 8,337,463 Under 35 U.S.C. 312 and 37 C.F.R. 42.104; USPTO PTAB; *Becton, Dickinson and Company v. B. Braun Melsungen AG*; Jun. 16, 2017; 76 pages.
Case IPR2017-01585, U.S. Pat. No. 8,337,463 B2; Notice of Filing Date Accorded to Petition and Time for Filing Patent Owner Preliminary Response; USPTO PTAB; *Becton, Dickinson and Company v. B. Braun Melsungen AG*; Jun. 22, 2017; Paper No. 4; 5 pages.
Case IPR2017-01585, U.S. Pat. No. 8,337,463 B2; Decision Denying Institution of Inter Partes Review 37 C.F.R. 42.108; USPTO PTAB; *Becton, Dickinson and Company v. B. Braun Melsungen AG*; Dec. 15, 2017; Paper No. 8; 31 pages.
IPR Trial No. IPR2017-01583, U.S. Pat. No. 8,333,735; Petition for Inter Partes Review of Claims 1, 9, 10, 11, 18, 19, 24 of U.S. Pat. No. 8,333,735 Under 35 U.S.C. 312 and 37 C.F.R. 42.104; USPTO PTAB; *Becton, Dickinson and Company v. B. Braun Melsungen AG*; Jun. 16, 2017; 90 pages.
IPR Trial No. IPR2017-01583, U.S. Pat. No. 8,333,735; Declaration of Jack Griffis, III Regarding U.S. Pat. No. 8,333,735, Claims 1, 9, 10, 11, 18, 19, 24; USPTO PTAB; *Becton, Dickinson and Company v. B. Braun Melsungen AG*; Jun. 16, 2017; 282 pages.
Case IPR2017-01583, U.S. Pat. No. 8,333,735 B2; Notice of Filing Date Accorded to Petition and Time for Filing Patent Owner

(56) References Cited

OTHER PUBLICATIONS

Preliminary Response; USPTO PTAB; *Becton, Dickinson and Company v. B. Braun Melsungen AG*; Jun. 20, 2017; Paper No. 4; 5 pages.
IPR Trial No. IPR2017-01584, U.S. Pat. No. 8,540,728; Petition for Inter Partes Review of Claims 1, 2, 9, 10, 24, 27, 28 of U.S. Pat. No. 8,540,728 Under 35 U.S.C. 312 and 37 C.F.R. 42.104; USPTO PTAB; *Becton, Dickinson and Company v. B. Braun Melsungen AG*; Jun. 16, 2017; 70 pages.
IPR Trial No. IPR2017-01584, U.S. Pat. No. 8,540,728; Declaration of Jack Griffis, III Regarding U.S. Pat. No. 8,540,728, Claims 1, 2, 9, 10, 24, 27, 28; USPTO PTAB; *Becton, Dickinson and Company v. B. Braun Melsungen AG*; Jun. 16, 2017; 182 pages.
Case IPR2017-01584, U.S. Pat. No. 8,540,728 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
IPR Trial No. IPR2017-01587, U.S. Pat. No. 9,149,626; Petition for Inter Partes Review of Claims 11, 20 of U.S. Pat. No. 9,149,626 Under 35 U.S.C. 312 and 37 C.F.R. 42.104; USPTO PTAB; *Becton, Dickinson and Company v. B. Braun Melsungen AG*; Jun. 16, 2017; 62 pages.
Case IPR2017-01587, U.S. Pat. No. 9,149,626 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
IPR Trial No. IPR2017-01588, U.S. Pat. No. 8,460,247; Petition for Inter Partes Review of Claims 12, 13, 20, 22, 23, 29 of U.S. Pat. No. 8,460,247 Under 35 U.S.C. 312 and 37 C.F.R. 42.104; USPTO PTAB; *Becton, Dickinson and Company v. B. Braun Melsungen AG*; Jun. 16, 2017; 84 pages.
IPR Trial No. IPR2017-01588, U.S. Pat. No. 8,460,247; Declaration of Jack Griffis, III Regarding U.S. Pat. No. 8,460,247, Claims 12,13, 20-23, 29; USPTO PTAB; *Becton, Dickinson and Company v. B. Braun Melsungen AG*; Jun. 16, 2017; 118 pages.
Case IPR2017-01588, U.S. Pat. No. 8,460,247 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01588, U.S. Pat. No. 8,460,247 B2; Decision Institution of Inter Partes Review 37 C.F.R. 42.108; USPTO PTAB; *Becton, Dickinson and Company v. B. Braun Melsungen AG*, Dec. 21, 2017; Paper No. 8; 44 pages.
IPR Trial No. IPR2017-01589, U.S. Pat. No. 8,597,249; Petition for Inter Partes Review of Claims 1 and 4 of U.S. Pat. No. 8,597,249 Under 37 C.F.R. 312 and 37 C.F.R. 42,104; USPTO PTAB; *Becton, Dickinson and Company v. B. Braun Melsungen AG*; Jun. 16, 2017; 57 pages.
IPR Trial No. IPR2017-01589, U.S. Pat. No. 8,597,249; Declaration of Jack Griffis, III Regarding U.S. Pat. No. 8,597,249, Claims 1 and 4; USPTO PTAB; *Becton, Dickinson and Company v. B. Braun Melsungen AG*; Jun. 16, 2017; 78 pages.
Case IPR2017-01589, U.S. Pat. No. 8,597,249 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01589, U.S. Pat. No. 8,597,249 B2; Decision Institution of Inter Partes Review 37 C.F.R. 42.108; USPTO PTAB; *Becton, Dickinson and Company v. B. Braun Melsungen AG*, Jan. 12, 2018; Paper No. 8; 39 pages.
IPR Trial No. IPR2017-01590, U.S. Pat. No. 9,370,641; Petition for Inter Partes Review of Claims 15, 17, 18, 20, 22 of U.S. Pat. No. 9,370,641 Under 35 U.S.C. 312 and 37 C.F.R. 42.104; USPTO PTAB; *Becton, Dickinson and Company v. B. Braun Melsungen AG*; Jun. 16, 2017; 56 pages.
Case IPR2017-01590, Patent 9,370,641 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01590, Patent 9,370,641 B2; Decision Institution of Inter Partes Review 37 C.F.R. 42.108; USPTO PTAB; *Becton, Dickinson and Company v. B. Braun Melsungen AG*, Jan. 11, 2018; Paper No. 9; 30 pages.
Civil Action No. 1:16-cv-411-RGA; Memorandum Opinion; in the United States District Court for the District of Delaware; *B. Braun Melsungen AG, B. Braun Medical Industries SDN. BHD, and B. Braun Medical, Inc. v. Becton, Dickinson and Company and Becton, Dickinson Infusion Therapy Systems, Inc.*; Aug. 7, 2017; 24 pages.
First Examination Report on corresponding foreign application (AU Application No. 2016269475) from the Australian Intellectual Property Office dated Jul. 16, 2018.
First Examination Report on corresponding foreign application (AU Application No. 2016269477) from the Australian Intellectual Property Office dated Jul. 16, 2018.
Notice of Opposition to a European Patent, dated Oct. 21, 2008, European Patent Office, Opposed Patent No. EP 1 545 681, B. Braun Melsungen AG.
Submission of Proprietor, Feb. 4, 2013, Opposition Against EP 1 545 681.
Submission of Proprietor, Apr. 19, 2013, Opposition Against EP 1 545 681.
Expert Opinion by Dr. Hans Haindl dated Apr. 17, 2013 incl. Annexes I-III (BB2).
Submission of Proprietor, Feb. 18, 2014, Opposition Against EP 1 545 681.
Expert Opinion by Dr. Hans Haindl dated Feb. 16, 2014 incl Annexes 1 to 4a, 4b (BB3).
Excerpt from the internet "Devices that may Interfere with Pacemakers", 2013 (BB4).
Excerpt from the online medical textbook "Thieme", p. 1, paragraphs under titles "Inwiefern können elektronische Geräte einen Herzschrittmacher (HSM) beeinflussen?", "Inwiefern beeinflussen Handys Herzschrittmacher?", and Wie können HSM durch Magnetfelder beeinflusst werden (BB5).
Decision in the amended version of the High Court of Malaya at Kuala Lumpur dated Jan. 8, 2013 (Civil Suit No. D-221P-53/2010) (BB6).
Re-Examination Report dated Oct. 17, 2013 of AU 2003246358 (BB7 incl. attachment I).
Submission of Proprietor, Aug. 1, 2014, Opposition Against EP 1 545 681.
Affidavit by Greg Noonan dated Jul. 31, 2014 (BB15).
Decision of Board of Appeal dated Oct. 8, 2014, rejecting appeal.
Search Report from DE Intellectual Property Office on corresponding DE application (202 10 394.3) dated Jun. 17, 2003.
AU Statement of Grounds and Particulars dated Feb. 19, 2010, Opposition to Patent Application No. 2003246358.
First Examination Report on corresponding foreign application (AU Application No. 2009238275) from the Australian Intellectual Property Office dated Feb. 14, 2012.
Notice of Acceptance on corresponding foreign application (AU Application No. 2009238275) from the Australian Intellectual Property Office dated Feb. 27, 2013.
English Translation of Office Action on corresponding foreign application (JP Application No. 2004-518674) from the Japan Patent Office dated Jun. 2, 2009.
Office Action on corresponding foreign application (MX Application No. PA/a/2004/012830) from the Mexican Patent Office dated Aug. 7, 2007.
Office Action on corresponding foreign application (MX Application No. PA/a/2004/012830) from the Mexican Patent Office dated Dec. 7, 2007.
Office Action on corresponding foreign application (MX Application No. PA/a/2004/012830) from the Mexican Patent Office dated Mar. 31, 2008.
Office Action on corresponding foreign application (MX Application No. MX/a/2008/007111) from the Mexican Patent Office dated Apr. 29, 2010.

(56) References Cited

OTHER PUBLICATIONS

Office Action on corresponding foreign application (MX Application No. MX/a/2010/012000) from the Mexican Patent Office dated Feb. 27, 2014.
Office Action on corresponding foreign application (MX Application No. MX/a/2013/002156) from the Mexican Patent Office dated Aug. 18, 2015.
First Examination Report on corresponding foreign application (AU Application No. 2013201814) from the Australian Intellectual Property Office dated Oct. 4, 2013.

* cited by examiner

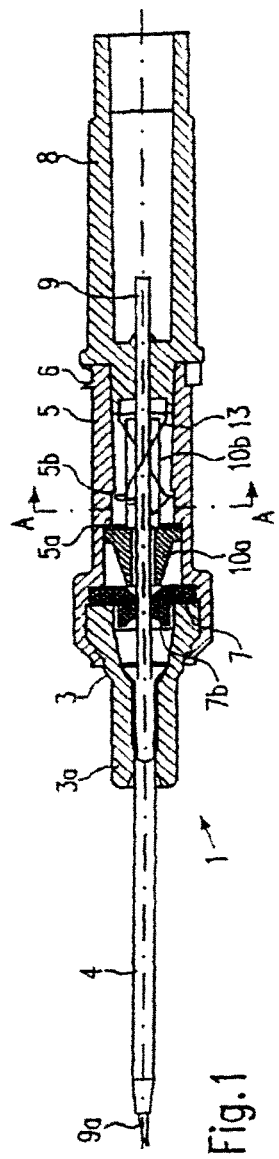
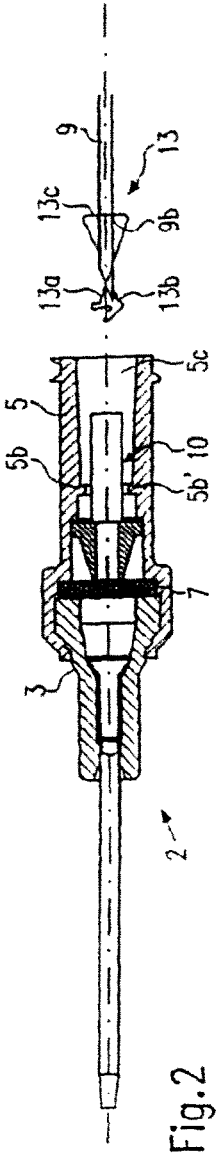
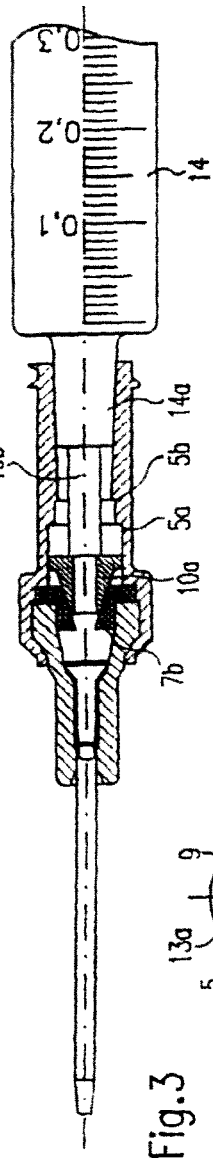
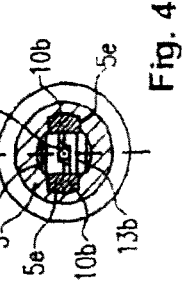
Fig.1
Fig.2
Fig.3
Fig.4

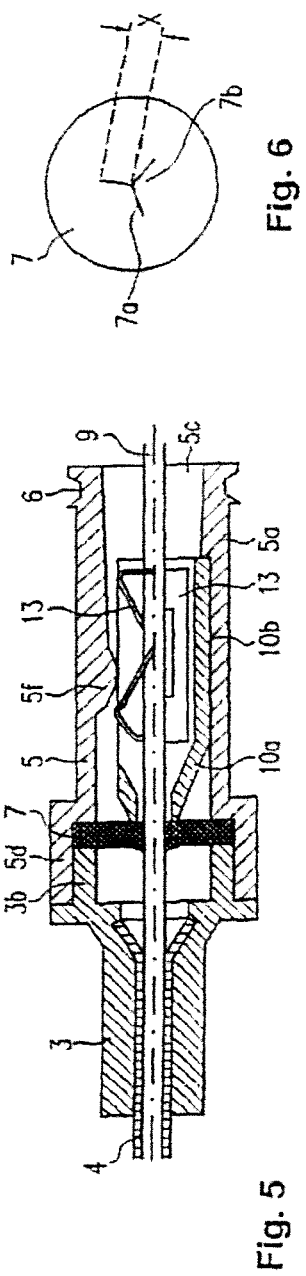
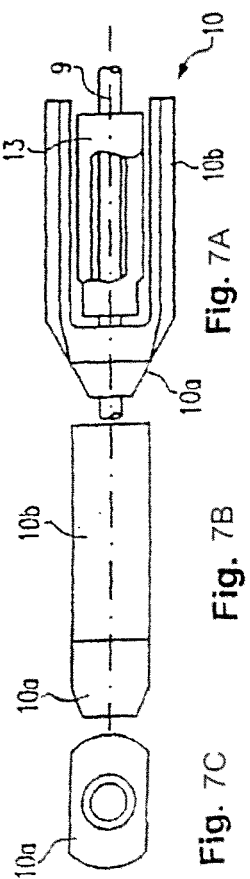
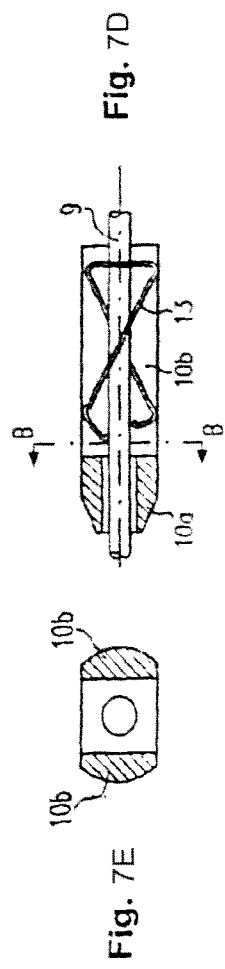
Fig. 5
Fig. 6
Fig. 7A
Fig. 7B
Fig. 7C
Fig. 7D
Fig. 7E

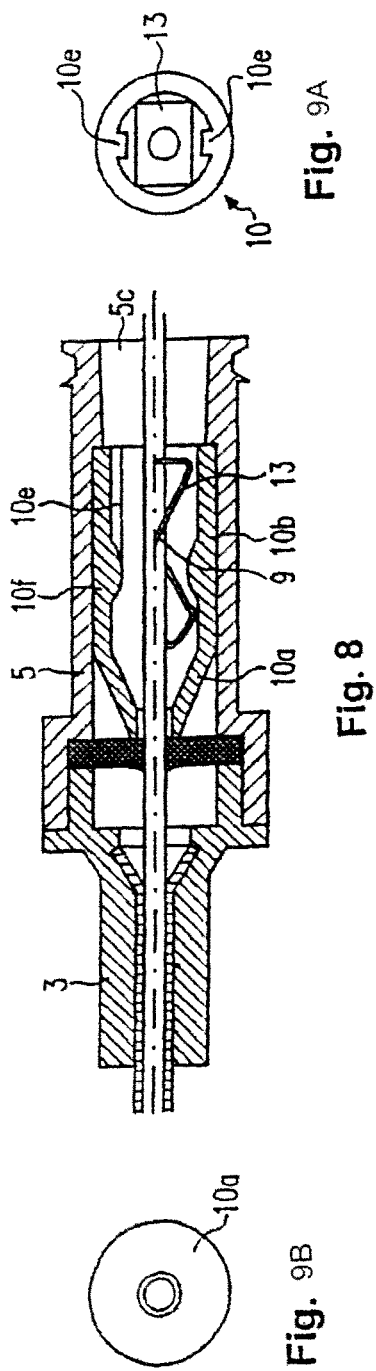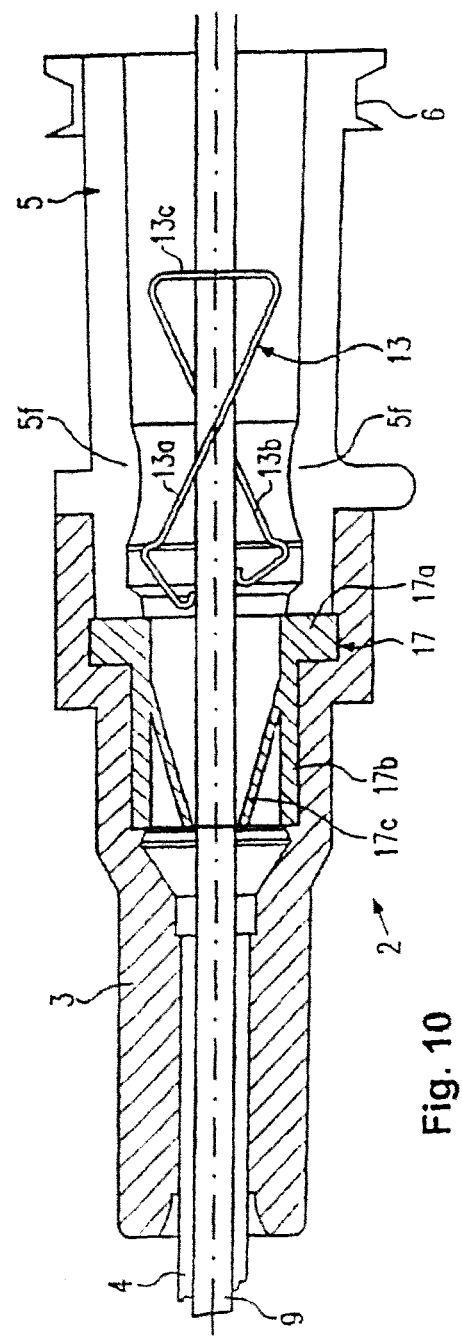

CATHETER INSERTION DEVICE

FIELD

Device, system, and method for a catheter insertion device are generally discussed herein with specific reference to catheter device having a valve opener and a valve.

BACKGROUND

A device of this kind is known from EP 352 928, wherein in a hollow catheter hub a needle guard element is arranged. On withdrawal of the hollow needle from the catheter over an engaging means near the tip of the hollow needle, the needle guard element engages with the engaging means and covers the tip when the hollow needle is separated from the catheter. In this design, after withdrawal of the hollow needle from the catheter, through this catheter blood can issue with which the operating personnel can come into contact.

The invention is based on the object of designing a catheter insertion device of the type described above such that an outflow of blood from the catheter is prevented after removal of the hollow needle with the needle guard element.

SUMMARY

This object is solved according to the invention by the features in the characterizing part of claim 1. In the ready position, a check valve is arranged in the catheter hub between the catheter and the needle guard element. Through this valve the hollow needle extends, so that after withdrawal of the hollow needle from the catheter the latter can be reliably closed such that an outflow of blood is prevented, while simultaneously the tip of the hollow needle is securely covered by the needle guard element so that the operating personnel cannot injure themselves on the needle tip.

BRIEF DESCRIPTION OF THE DRAWINGS

Exemplary embodiments of the invention are explained in more detail below with reference to the drawing, in which:

FIG. 1 shows a longitudinal section through a catheter insertion device in the ready position, FIG. 2 shows the catheter insertion device with the hollow needle removed, FIG. 3 shows the device with an attached syringe, FIG. 4 shows a sectional view along the line A-A in FIG. 1, FIG. 5 shows a longitudinal section through another embodiment, FIG. 6 shows a view of the valve disc, FIGS. 7A, 7B, 7C, 7D, and 7E show different views of a valve actuating element, FIG. 8 shows a longitudinal section through a further embodiment, FIGS. 9A and 9B show front views of the valve actuating element of FIG. 8, and FIG. 10 shows a longitudinal section through a further embodiment.

DETAILED DESCRIPTION

FIG. 1 shows a catheter insertion device 1 having a catheter hub 2 which has a two-part form in the embodiment. A distal hub element 3 of the catheter hub has a holding section 3a in which a catheter 4 is press-fitted. The proximal end of the hub element 3 has an enlarged diameter with regard to the distal end and forms a connecting section with a hub element 5 whose distal end overlaps the proximal end of the hub element 3 and which is provided at its proximal end with a Luer thread 6. Between the two hub elements 3 and 5, a check valve in the form of a valve disc 7 is inserted and is fixed in place by the two hub elements 3 and 5.

In the ready position according to FIG. 1, there is inserted in the catheter hub 2 a needle hub 8 to which a hollow needle 9 is fixed which extends through the valve disc 7 and the catheter 4 so that the needle tip 9a is exposed. Between needle hub 8 and valve disc 7 there is displaceably arranged in the proximal hub element 5 a valve actuating element 10 which has a truncated cone-shaped locating section 10a which serves to open the valve disc 7, as FIG. 3 shows. On the proximal side, a plunger section 10b adjoins the locating section 10a and has a hollow space for receiving a needle guard element 13. In the embodiment shown, the plunger section 10b is formed by two spaced plungers between which the needle guard element in the form of a spring clip 13 is inserted, as shown in the cross-sectional view in FIG. 4.

On withdrawal of the hollow needle 9 from the catheter hub 2, an engaging means 9b (FIG. 2), provided near the needle tip 9a and having the form of a radial projection on the hollow needle which can be formed by light crimping, engages with the outer circumference of a bore in the rear wall 13c of the spring clip 13, so that the spring clip 13 is removed from the catheter hub with the needle 9, while simultaneously the spring arms 13a and 13b of the spring clip cover the needle tip, completely protecting and blocking it. In this separated position shown in FIG. 2, the valve disc 7, due to its elasticity, closes the through-hole for the hollow needle 9 so that no blood can flow out through the catheter 4. As FIG. 6 shows, the valve disc is provided for example with three slits 7a starting from the middle and extending radially over a short section X, forming elastic flaps 7b therebetween which can be expanded by the hollow needle.

FIG. 3 shows the insertion of a syringe 14 in the catheter hub 2, wherein the neck portion 14a of the syringe comes to abut on the plunger section 10b of the valve actuating element 10 and presses it against the valve disc 7, so that the truncated cone-shaped locating section 10a outwardly displaces the flaps 7b of the valve disc and thereby opens the valve, so that a liquid can be inserted from the syringe 14 into the catheter 4.

The incline of the truncated cone on the locating section 10a and the displacement path of the actuating element 10 relative to the valve disc 7 are designed such that due to the elasticity of the material of the valve disc 7, the flaps 7b displace the locating section 10a to the right in FIG. 3 when the syringe 14 is removed from the catheter hub 2. Hereby, the valve disc 7 is automatically closed, as the position in FIG. 2 shows.

In the hub element 5, there is formed by a shoulder 5a a stop for the actuating element 10, to define the position of the actuating element in the separated position in FIG. 2. Hereby, the truncated cone-shaped locating section 10a lies near the stop 5a, while its distal end abuts on the valve disc 7 as shown in FIG. 2. The radial slits 7a of the valve disc 7 are designed such that in the ready position in FIG. 1, the flaps 7b are bent radially upwards less than in the open position by the locating section 10a in FIG. 3.

As the cross-sectional view in FIG. 4 shows, the two plungers 10b of the valve actuating element 10 are guided in longitudinal grooves 5e of the hub element 5 and they project radially inwards into the bore 5c of the hub element 5, so that they form an abutting surface for the neck portion 14a of the syringe 14. The bore 5c in the hub element 5 is formed slightly conically corresponding to the conical neck portion 14a of a syringe.

On the inner circumference of the bore 5c of the hub element 5, a further shoulder 5b having a smaller diameter is formed, on which the radially outer areas of the spring arms 13a and 13b abut in the ready position in FIG. 1. Hereby, the spring clip 13 is fixed in its position in the hub element 5. When the needle hub 8 with the hollow needle 9 is removed from the catheter hub 2, first the spring clip 13 is held on the shoulder 5b by abutting until the radial projection 9b comes to abut on the rear wall 13c of the spring clip. In this position, the two spring arms 13a, 13b can be released from the shoulder 5b and spring back inwards to cover the needle tip, as FIG. 2 shows, whereupon the spring clip 13 with the hollow needle 9 can be removed from the catheter hub.

In the embodiment according to FIGS. 1 to 3, the distal end section of the hub element 5 is shrunk, welded or bonded onto the proximal end section of the hub element 3 after the valve actuating element 10 and the valve disc 7 are inserted in the hub element 5. It is also possible to join the two hub elements 3 and 5 to one another, for example by a thread which is secured against loosening after assembly. The spring clip 13 is inserted together with the hollow needle 9 in the bore 5c of the hub element 5 during assembly, wherein the radially outer areas of the spring arms 13a, 13b snap in at the shoulder 5b under elastic deformation.

Preferably, in front of the shoulder 5b a projection 5b' can be formed in the bore 5c of the hub element, as shown in FIG. 2. Hereby the snap-in and holding effect of the spring clip 13 is increased.

FIG. 5 shows a modified embodiment of the connection of the two hub elements 3 and 5, in which two cylindrical sections 3b and 5d engage in one another. A thread can be provided between these two cylindrical sections. However, it is also possible to bond or weld these two sections.

In this embodiment, the valve actuating element 10 is also modified in relation to the embodiment of FIGS. 1 to 3. FIG. 7A shows a side view of the approximately U-shaped actuating element 10 with the spring clip 13 inserted therein. As the side view rotated by 90° in FIG. 7B shows, the locating section 10a is partly flattened on opposite sides so that the width of the plunger sections 10b extends into the locating section 10a. FIG. 7C is a front view from the left in FIG. 7B and shows the flattened structure of the locating section 10a. FIG. 7D is a sectional view along the central line in FIG. 7B. FIG. 7E shows a section through the valve actuating element 10 along the line B-B in FIG. 7D.

FIG. 5 shows the lower half of the valve actuating element 10 corresponding to the view in FIG. 7A, and the upper half in a sectional view rotated by 90° corresponding to FIG. 7B. The shoulder 5a for positioning the valve actuating element 10 in the hub element 5 is hereby formed on the ends of the diametrically opposite grooves 5e (FIG. 4), so that the proximal ends of the plunger sections 10b abut on the shoulders 5a. Corresponding to the shoulder 5b in FIGS. 1 to 3 in the embodiment in FIG. 5, there is formed on the hub element 5 a projection 5f which projects inwards at diametrically opposite positions on the bore 5c of the hub element 5 and fixes the spring clip 13 in the hub element 5 until the spring arms 13a, 13b spring inwards over the needle tip and the spring clip with the hollow needle 9 is removed from the catheter hub.

FIG. 8 shows a modified embodiment having a hollow cylindrical valve actuating element 10 on whose inner circumference a projection 10f is formed for positioning the spring clip 13 inside the valve actuating element 10. FIG. 9A shows a front view of the valve actuating element 10 from the right and FIG. 9B shows a front view from the left in FIG. 8, wherein for locating the neck portion 14a of a syringe 14, in this embodiment radially inwardly projecting ribs 10e are formed which protrude radially into the bore 5c of the hub element 5, as the upper half of the valve actuating element in FIG. 8 shows, in which the sectional view of the lower half of the valve actuating element 10 is shown rotated by 90° in relation to the upper half.

FIG. 10 shows a modified embodiment wherein between the two hub elements 3 and 5 a check valve 17 is inserted, which has a hollow cylindrical section 17b starting from a flange section 17a and abutting on the inner circumference of the hub element 3. From the inner circumference near the flange section 17a there start two opposite flaps 17c, which abut on the outer circumference of the hollow needle 9 in the ready position in FIG. 10. When the needle 9 is removed from the catheter hub 2, the elastically deformed flaps 17c move inwards and close the valve. In this embodiment, an actuating element for opening the valve 17 is not necessary, because the pressure of the fluid from the syringe 14 displaces the flaps 17c radially outwards so that the liquid can flow out through the valve 17. In this embodiment of a check valve, a so-called duck-bill valve is concerned, whose construction is in itself known.

In FIG. 10, in order to allow the spring clip 13 to be held in the catheter hub during withdrawal of the hollow needle 9 from the catheter hub 2 until the radial projection 9b on the hollow needle engages with the rear wall 13c to cover the needle tip, in this embodiment there is formed on the inner circumference of the proximal hub element 5 a projection 5f which extends radially inwards and on which the radially outer areas of the spring arms 13a and 13b come to abut and hold the spring clip until the spring arms spring back radially inwards to cover the needle tip. The inner diameter of the projection 5f is designed only slightly smaller than the maximum radial dimension at the spring arms 13a and 13b, so that during assembly the spring clip 13 can be inserted by slight pressure into the position in the catheter hub as shown in FIG. 10.

In the embodiment of a catheter insertion device according to FIGS. 1 to 9, in the position of the valve actuating element 10 in FIG. 2 the valve disc 7 can be opened by low pressure produced by the syringe 4 for drawing off liquid from the catheter, wherein the elastic flaps 7b are bent upward by the low pressure. In the embodiment of FIG. 10, a drawing-off of liquid from the catheter is not possible, because the duck-bill valve does not open when there is low pressure on the proximal side.

It is convenient to fabricate the check valve in the form of a valve disc 7 or of the flap valve 17 from elastic silicon, while a correspondingly rigid plastic material is used for the hub elements 3 and 5 and for the valve actuating element 10.

What is claimed is:
1. A catheter insertion device comprising:
   a catheter hub comprising a body having an interior surface defining a bore having a groove on the interior surface; said bore comprising an opening at a proximal end and a catheter tube attached at a distal end;
   a valve located inside the bore of the catheter hub for blocking fluid flow therethrough and remaining inside the bore in a ready position and a needle guarded position;

a valve actuating element slidably disposed in the bore of the catheter hub; said valve actuating element comprising a locating section and a plunger section extending from the locating section;

a needle having a needle shaft defining a needle axis projecting distally of an end of a needle hub, said needle projecting through the catheter tube and comprising a needle tip extending out a distal opening of the catheter tube;

a needle guard slidably mounted relative to the needle so that the needle tip is guarded by the needle guard when the needle tip is removed from the catheter hub; and wherein the valve actuating element is guided in the groove of the bore and projects radially into the bore and said plunger section provides an abutting surface for a conical neck portion.

2. The catheter insertion device of claim 1, wherein the plunger section comprises two spaced apart plungers.

3. The catheter insertion device of claim 2, wherein the needle guard is located between the two spaced apart plungers.

4. The catheter insertion device of claim 2, wherein the groove comprises two spaced apart longitudinal grooves and the two spaced apart plungers are located in the two spaced apart longitudinal grooves.

5. The catheter insertion device of claim 1, wherein the valve actuating element comprises a flange abutting a shoulder in the bore of the catheter hub.

6. The catheter insertion device of claim 1, wherein the needle comprises a lateral projection for engaging a perimeter defining an opening on a proximal wall of the needle guard.

7. The catheter insertion device of claim 1, wherein the catheter hub comprises a first hub section attached to a second hub section.

8. The catheter insertion device of claim 1, wherein the valve comprises three slits defining three flaps.

9. A method for assembling a catheter insertion device comprising:

forming a catheter hub comprising a body having an interior surface defining a bore having a groove on the interior surface; said bore comprising an opening at a proximal end and a catheter tube attached at a distal end;

positioning a valve inside the bore of the catheter hub for blocking fluid flow therethrough such that the valve remains inside the bore in a ready position and in a needle guarded position;

positioning a valve actuating element slidingly in the bore of the catheter hub; said valve actuating element comprising a locating section and a plunger section extending from the locating section;

projecting a needle having a needle shaft defining a needle axis distally of an end of a needle hub and projecting through the catheter tube so that a needle tip of the needle extends out a distal opening of the catheter tube;

mounting a needle guard slidingly relative to the needle so that the needle tip is guarded by the needle guard when the needle tip is removed from the catheter hub; and wherein the valve actuating element is guided in the groove of the bore and projects radially into the bore and said plunger section providing an abutting surface for a conical neck portion.

10. The method of claim 9, wherein the catheter hub comprises a first hub section attached to a second hub section.

11. The method of claim 9, wherein the plunger section comprises two spaced apart plungers and the needle guard is located between the two spaced apart plungers.

12. The method of claim 9, wherein the groove comprises two spaced apart longitudinal grooves and the plunger section comprises two spaced apart plungers, and wherein the two spaced apart plungers are located in the two spaced apart longitudinal grooves.

13. The method of claim 9, wherein the needle guard engages the interior surface of the catheter hub in the ready position.

14. A catheter insertion device comprising:

a catheter hub comprising a groove formed in a bore having an opening at a proximal end;

a catheter tube having a distal end opening extending distally of the catheter hub;

a needle having a needle shaft with a needle tip projecting distally of an end of a needle hub, said needle projecting through the catheter tube and the needle tip projecting distally of the distal end opening of the catheter tube;

a valve positioned inside the bore of the catheter hub, said valve obstructing fluid flow and comprises a plurality of slits defining a plurality of flaps; said valve remaining inside the bore of the catheter hub when the needle is removed from the catheter tube and the catheter hub;

a valve actuating element slidingly disposed in the bore of the catheter hub to actuate the valve, the valve actuating element comprising a tapered nose section structured to push the valve to open the plurality of slits and two spaced apart plungers extending proximally of the nose section and each of the two spaced apart plungers are disposed in the groove; and a needle guard slidably mounted relative to the needle so that the needle tip is guarded by the needle guard when the needle tip is removed from the catheter hub.

15. The catheter insertion device of claim 14, wherein the needle guard is located inside the bore of the catheter hub.

16. The catheter insertion device of claim 15, wherein the needle guard comprises a proximal wall with a perimeter defining an opening and two resilient arms.

17. The catheter insertion device of claim 16, wherein the needle guard is located between the two spaced apart plungers.

18. The catheter insertion device of claim 16, further comprising a radial projection on the needle for engaging the proximal wall when the needle is removed from the catheter hub.

19. The catheter insertion device of claim 14, wherein the valve actuating element comprises a flange abutting a shoulder in the bore of the catheter hub.

20. The catheter insertion device of claim 14, wherein the catheter hub comprises a first hub section attached to a second hub section.

* * * * *

UNITED STATES PATENT AND TRADEMARK OFFICE
CERTIFICATE OF CORRECTION

PATENT NO. : 10,080,869 B2
APPLICATION NO. : 14/860253
DATED : September 25, 2018
INVENTOR(S) : Woehr et al.

It is certified that error appears in the above-identified patent and that said Letters Patent is hereby corrected as shown below:

On the Title Page

In page 4, Column 2 (item (56) Other Publications), Line 35, after "Report" insert -- of --.

Signed and Sealed this
Sixteenth Day of August, 2022

Katherine Kelly Vidal
*Director of the United States Patent and Trademark Office*